US012636298B2

(12) United States Patent
Loake et al.

(10) Patent No.: US 12,636,298 B2
(45) Date of Patent: May 26, 2026

(54) COMPOSITION WITH L-THEANINE AND FRUCTOOLIGOSACCHARIDES FOR HUMAN MEMORY ENHANCEMENT

(71) Applicant: HARKE Pharma GmbH, Mülheim an der Ruhr (DE)

(72) Inventors: Gary J. Loake, Edinburgh (GB); Yuan Li, Edinburgh (GB)

(73) Assignee: HARKE Pharma GmbH, Mulheim an der Ruhr (DE)

( * ) Notice: Subject to any disclaimer, the term of this patent is extended or adjusted under 35 U.S.C. 154(b) by 868 days.

(21) Appl. No.: 17/787,854

(22) PCT Filed: Dec. 17, 2020

(86) PCT No.: PCT/EP2020/086897

§ 371 (c)(1),
(2) Date: Jun. 21, 2022

(87) PCT Pub. No.: WO2021/123071

PCT Pub. Date: Jun. 24, 2021

(65) Prior Publication Data

US 2023/0048802 A1     Feb. 16, 2023

(30) Foreign Application Priority Data

Dec. 20, 2019    (GB) ...................................... 1918997

(51) Int. Cl.
| | |
|---|---|
| *A61K 31/702* | (2006.01) |
| *A23L 33/105* | (2016.01) |
| *A23L 33/155* | (2016.01) |
| *A23L 33/16* | (2016.01) |
| *A23L 33/175* | (2016.01) |
| *A23L 33/21* | (2016.01) |
| *A61K 31/07* | (2006.01) |
| *A61K 31/145* | (2006.01) |
| *A61K 31/198* | (2006.01) |
| *A61K 31/355* | (2006.01) |
| *A61K 31/375* | (2006.01) |
| *A61K 31/593* | (2006.01) |
| *A61K 33/00* | (2006.01) |
| *A61K 33/06* | (2006.01) |
| *A61K 45/06* | (2006.01) |
| *A61P 25/28* | (2006.01) |

(52) U.S. Cl.
CPC .......... *A61K 31/702* (2013.01); *A23L 33/105* (2016.08); *A23L 33/155* (2016.08); *A23L 33/16* (2016.08); *A23L 33/175* (2016.08); *A23L 33/21* (2016.08); *A61K 31/07* (2013.01); *A61K 31/145* (2013.01); *A61K 31/198* (2013.01); *A61K 31/355* (2013.01); *A61K 31/375* (2013.01); *A61K 31/593* (2013.01); *A61K 33/00* (2013.01); *A61K 33/06* (2013.01); *A61K 45/06* (2013.01); *A61P 25/28* (2018.01); *A23V 2002/00* (2013.01)

(58) Field of Classification Search
None
See application file for complete search history.

(56) References Cited

U.S. PATENT DOCUMENTS

2004/0171624 A1     9/2004   Ozeki et al.

FOREIGN PATENT DOCUMENTS

| | | | | |
|---|---|---|---|---|
| CN | 102030835 B | 4/2013 | | |
| CN | 103127163 A | * 6/2013 | ............... | A23L 1/09 |
| CN | 103 127 163 B | 6/2015 | | |
| CN | 107 927 732 A | 4/2018 | | |
| JP | 2018 012681 A | 1/2018 | | |

OTHER PUBLICATIONS

Chen, Diling et al. "Prebiotic Effect of Fructooligosaccharides from Morinda officinalis on Alzheimer's Disease in Rodent Models by Targeting the Microbiota-Gut-Brain Axis" Frontiers in Aging Neuroscience, Dec. 8, 2017, vol. 9, Article 403.
International Search Report and Written Opinion for PCT/EP2020/086897; Mailing date of Apr. 12, 2021.
Office Action in related IN Application 202217037985 dated Feb. 20, 2026.

* cited by examiner

*Primary Examiner* — Dale R Miller

(74) *Attorney, Agent, or Firm* — Fresh IP PLC; Clifford D. Hyra; Aubrey Y. Chen

(57) ABSTRACT

A composition comprising or consisting of L-theanine and one or more fructooligosaccharides, wherein the ratio of L-theanine to froctooligosaccharide(s) is of about 2:1 to 99:1. A composition in the form of a food or nutraceutical, and also in the form of a powder, granules, suspension, tablet, capsule, lozenge, bakery item, sweets, drink, beverage or oral preparation.

10 Claims, 2 Drawing Sheets

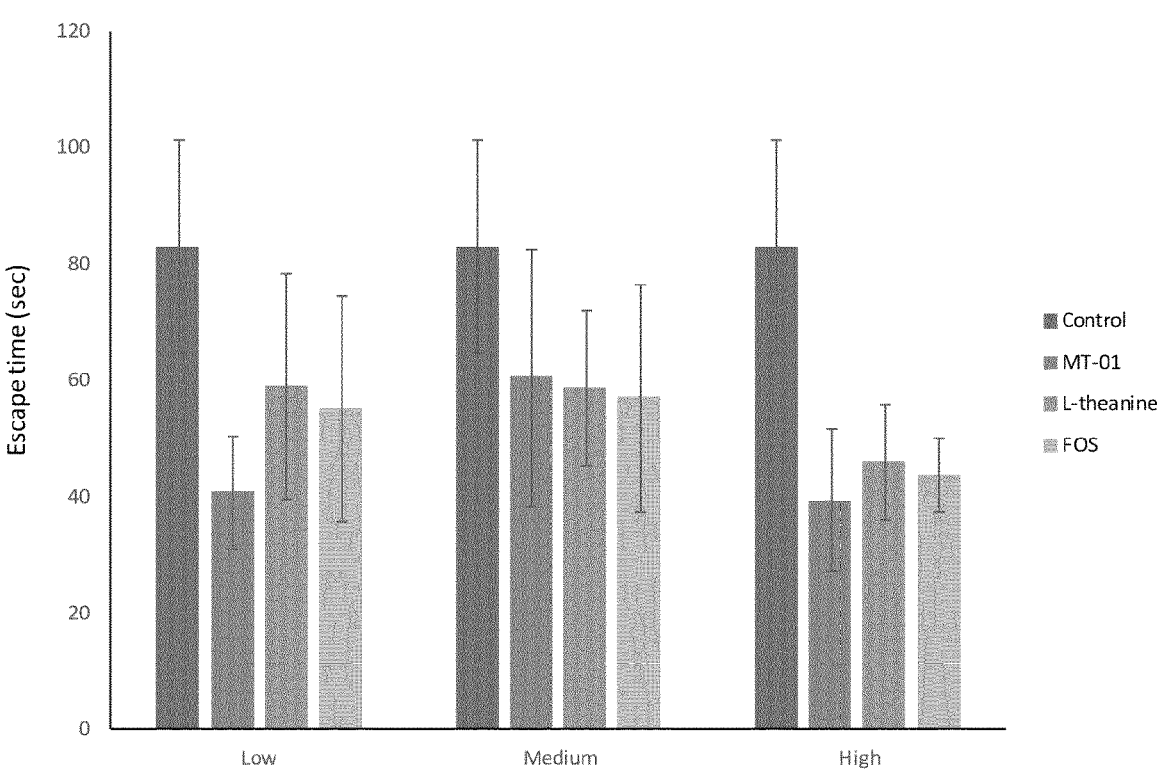
Fig. 1 a. Average escape time of mice during testing phase.
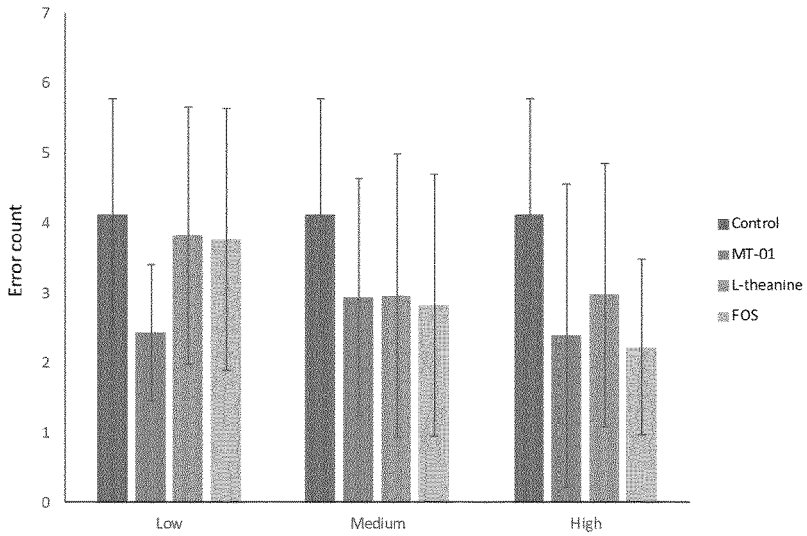
Fig 1 b. average error count for mice during testing phase in water maze test

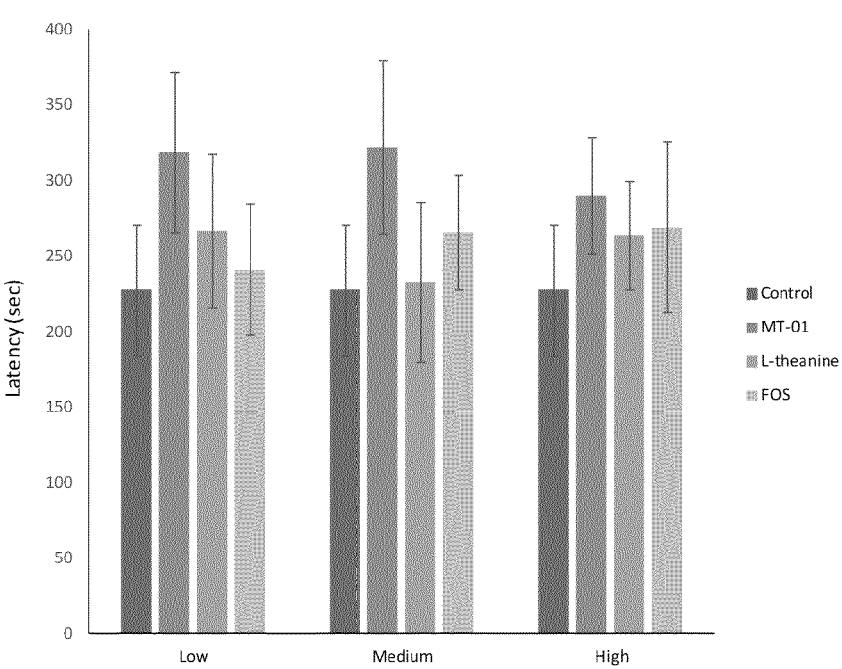
Fig 1 c. Average latency of mice in passive avoidance test during retention phase
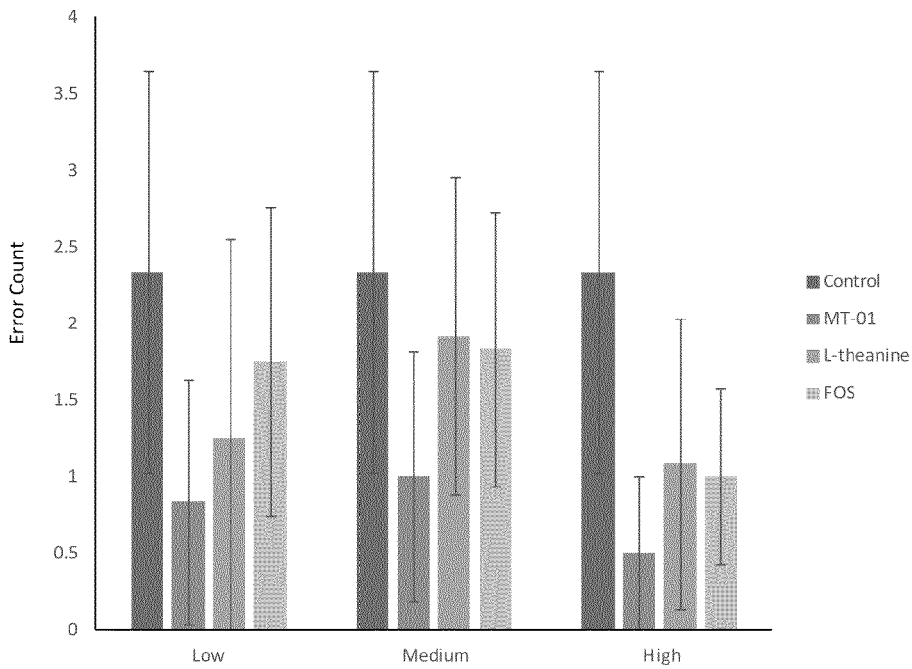
Fig 1 d. Average error count of mice in passive avoidance test during testing phase

COMPOSITION WITH L-THEANINE AND FRUCTOOLIGOSACCHARIDES FOR HUMAN MEMORY ENHANCEMENT

The present invention relates to a composition which may be taken orally as a dietary supplement or in a pharmaceutical or nutraceutical formulation. The composition may be employed to improve memory and may provide additional benefits such as enhancing concentration and calmness, reducing stress and anxiety and improving mood.

Memory is the faculty of the brain enabling information to be encoded, stored and retrieved as required to support cognitive performance (Sherwood, 2015). Memory is fundamental to experiences: it is the retention of information over time for influencing future action. In the absence of memory, personal identity, language and human relationships cannot be supported (Eysenck, 2012). Consequently, memory is central for human existence (Staniloiu, A. and Markowitsch, 2012).

Memory supports the retrieval of key information and skill sets that are stored in the brain, or the recall of precious moments that occurred in the past. Memory also organizes information effectively, facilitating successful retrieval. In general, we use short term memory to recall information we have stored recently (Cowan, 2001). In contrast, long term memory is employed to recall information that we have accumulated anytime in the recent past to childhood (Baddeley, 1966). Additionally, episodic memory is utilised to accumulate personal experiences: events that occurred at a particular place and time (Schacter, 2009).

Different areas of the brain including the hippocampus, the amygdala, the striatum, or the mammillary bodies are thought to be involved in specific types of memory. For example, the amygdala is thought to be key for emotional memory, whereas the hippocampus has been implicated in spatial and declarative learning (LaBar and Cabeza, 2006).

Forgetfulness is a common feature of aging adults. Typical causes of memory loss in older people are mild cognitive impairment, various types of dementia, and psychiatric illness, mainly depression. Around 10% of patients with mild cognitive impairment progress to dementia each year. Alzheimer's disease accounts for 60-80% of these cases (Ballard et al. 2011). Other common types of dementia are vascular, fronto-temporal, Lewy body, Parkinson's and mixed type dementia (Burns et al. 2009). There is evidence to suggest that dementia pathology is established before the onset of symptoms and thus mild cognitive impairment can be considered as a predementia stage (Burns et al. 2009).

It has been reported that a single consumption of a hot water diffusion extract from chicory root, rich in inulin, a long chain oligosaccharide polymer but also comprised of potentially many further oligosaccharides, in addition to other plant derived molecules, had a positive effect on human behaviour. In a laboratory study involving 50 participants, volunteers who consumed this complex mixture felt happier and had improved episodic memory (recall and recognition) but had no improvement of spatial memory or sustained attention (Smith et al. 2015). Thus, a water extract from chicory root containing a wide spectrum of plant derived molecules improved episodic memory, but not other aspects of the memory process.

Genetic causes of Alzheimer's disease (AD) include mutations in the amyloid precursor protein (APP), presenilin 1 (PS1) and presenilin 2 (PS2) genes (Hardy, 1997). The development of AD-like pathology is significantly enhanced in the absence of the function of these homologous genes in mice. Thus, APP/PS1 mice provide an animal model for AD.

In a further study, prolonged feeding of these APP/PS1 mice, which develop AD-like symptoms, with *Morinda officinalis* (Mo), a herbal plant, significantly ameliorated the development of AD in this animal model (Xin et al. 2018). Further, histological changes associated with the development of AD, including brain tissue swelling, neuronal apoptosis and expression of protein markers of AD, were also delayed and reduced. Comparison of the microbiome between Mo fed and non-Mo fed mice revealed some differences in the microbial community, suggesting Mo feeding might change the microbiome. However, differences between Mo fed and non-fed APP/PS1 mice could be detected within the first 24 hours, not sufficient time to enable significant changes in gut microflora, implying an alternative or at least an additional mechanism maybe be responsible. Nevertheless, this work suggested that consumption of Mo by APP/PS1 mice reduced the symptoms of AD in an animal model of this neurodegenerative disease.

L-theanine is an amino acid contained in green tea (*Camellia sinensis*), which has been suggested to have various psychotropic effects. In an open-label study, 8-week L-theanine administration was found to be safe and conveyed beneficial effects on depressive symptoms, anxiety, sleep disturbance and cognitive impairments in patients with major depressive disorders (Hidese et al. 2017). Further, this molecule is also suggested to have antidepressant-like effects in animals (Yin et al. 2011).

An additional study also explored the potential effect of phytochemicals from green tea on mood and cognition (Dietz and Dekker, 2017). The data suggested that caffeine with the addition of L-theanine had a positive effect on sustained attention and suppression of distraction.

Following investigations of various compounds and combinations we have now found a combination which is particularly effective in enhancing memory and in improving cognitive performance.

From a first aspect, the present invention provides a composition comprising L-theanine and one or more fructooligosaccharide(s).

Our findings establish that neither fructooligosaccharides nor L-theanine alone, especially in low or medium doses, improve mammalian memory following well-established memory tests. In contrast, as shown herein, a composition containing both fructooligosaccharides and L-theanine, especially in a ratio of about 2:1 to 99:1 L-theanine:fructooligosachharide(s), preferably a ratio of about 2:1, enhanced mammalian memory in a statistically significant fashion in a series of rodent memory assessments. Further, an independent, double-blind, human clinical trial, showed statistically significant improvement of clinical memory, associative learning, graphic memory, the recognition of meaningless images and portrait retrieval. Additionally, both memory quotient and total memory exhibited statistically significant enhancement following administration of the current invention. Therefore, administration of fructooligosaccharides and L-theanine especially in a ratio of about 2:1 to 99:1 L-theanine:fructooligosachharide(s) significantly improve human memory and cognitive performance, as scored by multiple clinical indicators.

Significantly, this composition can be administered to improve memory, of animals, e.g. of mammals, e.g. of humans, e.g. of healthy human adults. Further, this composition can also provide additional neurological benefits, including: anti-depression, reduction of anxiety, enhancement of concentration and promotion of calmness.

Our independent double-blind study established that neither specific fructooligosaccharides nor L-theanine, when administered individually, improved memory in a healthy mouse model system. However, when these molecules were added together, especially in a ratio of about 2:1 to 99:1 L-theanine:fructooligosachharide (s), a marked positive impact on memory, anti-depression, reduction of anxiety, enhancement of concentration and promotion of calmness were observed. In a subsequent independent, double-blind, healthy human clinical trial, similar results were recorded to those derived from the mouse model system.

The identified composition can be utilised to generate dietary supplements, e.g. in the form of drinks, tablets and capsules, or can be administered as a medicine.

From a further aspect the present invention provides a composition comprising one or more fructooligosaccharide and L-theanine for use as a medicament.

From a further aspect the present invention provides a composition comprising one or more fructooligosaccharides and L-theanine for use in enhancing memory.

From a further aspect the present invention provides a composition comprising one or more fructooligosaccharides and L-theanine for use in improving cognitive performance.

From a further aspect the present invention provides a composition comprising one or more fructooligosaccharides and L-theanine for treating age-related memory loss.

From a further aspect the present invention provides a composition comprising one or more fructooligosaccharides and L-theanine for cognitive therapy.

From a further aspect the present invention provides a composition comprising one or more fructooligosaccharides and L-theanine for use as a nootropic.

From a further aspect the present invention provides a composition comprising one or more fructooligosaccharides and L-theanine for stress management.

From a further aspect the present invention provides a composition comprising one or more fructooligosaccharides and L-theanine for sleeping improvement.

From a further aspect the present invention provides a composition comprising one or more fructooligosaccharides and L-theanine for the treatment of depression.

From a further aspect the present invention provides a composition comprising one or more fructooligosaccharides and L-theanine for the treatment of anxiety.

From a further aspect the present invention provides a composition comprising one or more fructooligosaccharides and L-theanine for enhancing concentration.

From a further aspect the present invention provides a composition comprising one or more fructooligosaccharides and L-theanine for promoting calmness.

From further aspects the present invention provides methods of treatment of the conditions and disorders listed above comprising the administration of an effective amount of a composition comprising one or more fructooligosaccharides and L-theanine to a patient in need thereof.

As well as the L-theanine and fructooligosaccharide(s) the composition may optionally further comprise other components, excipients or diluents.

The L-theanine and fructooligosaccharide(s) may be administered together or sequentially.

Optionally the fructooligosaccharide(s) may have a degree of polymerisation of from 3 to 9; in other words there may be between 3 and 9 fructose residues present in the fructooligosaccharide. The fructose is typically in the naturally-occurring form, i.e. D-fructose. As well as the 3 to 9 fructose residues present, glucose (e.g. one glucose residue, typically in its naturally occurring form, D-glucose) may also be present in the fructooligosaccharide. The fructooligosaccharide may comprise FructoseN and/or Glucose-FructoseN, where N is the degree of polymerisation of the fructose (between 3 and 9).

The relative amounts of the fructooligosaccharide(s) and L-theanine, by weight, are optionally within the range 1:99 to 99:1, optionally 1:50 to 50:1, optionally 1:20 to 20:1, optionally 1:10 to 10:1, optionally 1:5 to 5:1, optionally 1:4 to 4:1, optionally 1:2 to 2:1. However, best results were achieved for a ratio of about 2:1 to 99:1 L-theanine:fructooligosachharide(s), preferably about 2:1 to 50:1, more preferably about 2:1 to 20:1, even more preferably about 2:1 to 10:1, about 2:1 to 5:1 or about 2:1 to 4:1, and most preferably a ratio of about 2:1 L-theanine:fructooligosachharide (s).

A composition in accordance with the present invention may optionally contain between 1 and 1,000 mg (e.g. 10 to 500 mg) of fructooligosaccharide(s) and between 1 and 1,000 mg (e.g. 10 to 500 mg) of L-theanine. Further to our research, we have found that the composition in accordance with the present invention has rendered surprisingly good, synergic results as compared to administering the same doses of L-theanine or fructooligosaccharide(s) separately. This synergic, unexpected effect is especially achieved when the composition is administered to humans in doses of up to 300 mg/person/day fructooligosaccharide(s) and up to 600 mg/person/day L-theanine, preferably 140 to 280 mg/person/day fructooligosaccharide(s) and 280 to 580 mg/person/day L-theanine.

Our research has shown that, administered together, especially at the ratio of about 2:1 to 99:1, L-theanine and fructooligosaccharide(s) act synergistically in an unexpected manner, rendering superior results than expected from administering similar doses of L-theanine and fructooligosaccharide(s) separately. This effect was especially evident when the L-theanine and fructooligosaccharide(s) were administered in a ratio of about 2:1 in low to medium doses such as 250 to 600 mg/person/day of L-theanine and 120 to 300 mg/person/day of fructooligosaccharide(s).

The fructooligosaccharide(s) may include one or more trisaccharide, tetrasaccharide, pentasaccharide, hexasaccharide, heptaasaccharide, octasaccharide and nonasaccharide sugar molecules, and may consist of FructoseN and/or Glucose-FructoseN where N is between 3 and 9.

Fructooligosaccharide for use in the current invention can be extracted from the plant *Morinda officinalis* (Mo) and can be obtained as follows. Dried *Morinda officinalis* can be boiled with water, the boiled sample spun down by centrifugation and the resulting liquid collected and dried. The remaining brown extract can then be resuspended in water and loaded on to a chromatography column, the column washed with ethanol, and the ethanol wash-off collected, concentrated and spray dried to obtain the resulting purified fructooligosaccharide, confirmed by biochemical analysis.

L-theanine involved in the current invention can be extracted from *Camellia sinensis* or purchased commercially.

Additional pharmaceutical or food ingredients may further be added into the composition of the current invention as required. For example, amino acids (essential and/or non-essential), taurine, vitamins (such as vitamin A, B, C, D, E, etc.), metal supplements (such as sodium, potassium, calcium and magnesium), flavouring agents (sweeteners and flavours), fillers, lubricants and/or binders may be used. These additions are common ingredients used in functional foods which can be also added to the current invention to diversify potential commercial products based on the current invention.

The formulation combination may be prepared as follows: fructooligosaccharide(s) can be mixed with L— theanine together with any additives which are eligible to be used as pharmaceuticals or food supplements, if required. This composition can be made into products including drinks, powders, suspensions, granules, tablets, capsules or oral preparations There are further presented a series of examples of the invention, in connection also with the FIGURES, which represent:

FIG. 1a. Average escape time of mice during testing phase.

FIG. 1b. average error count for mice during testing phase in water maze test

FIG. 1c. Average latency of mice in passive avoidance test during retention phase FIG. 1d. Average error count of mice in passive avoidance test during testing phase The following examples are used to demonstrate possible formulations to utilise the present invention, and the application of the present invention is not restricted by the given examples. It should be noted that modifications or improvements can be made based on following examples; however, such modifications or improvements while not deviating from the application or effectiveness of the present invention are still covered by this patent.

Embodiment 1. A Composition Used to Improve Memory

Fructooligosaccharide: 10-500 mg
L-Theanine: 10-500 mg

The fructooligosaccharide(s) may include one or more trisaccharide, tetrasaccharide, pentasaccharide, hexasaccharide, heptaasaccharide, octasaccharide and nonasaccharide sugar molecules, and may consist of FructoseN and/or Glucose-FructoseN where N is between 3 and 9.

The above composition can be used to prepare orally administrable products including powders, granules, dry suspension, tablet, effervescent tablet, capsules, lozenges, sustained-release preparations, drinks, beverages and oral solutions using conventional techniques.

Embodiment 2. A Composition Used to Improve Memory

Fructooligosaccharide 10-500 mg
L-Theanine 10-500 mg
Vitamin B3: 1-10 mg
Vitamin B6:0.2-3 mg The fructooligosaccharide(s) may include one or more trisaccharide, tetrasaccharide, pentasaccharide, hexasaccharide, heptaasaccharide, octasaccharide and nonasaccharide sugar molecules, and may consist of FructoseN and/or Glucose-FructoseN where N is between 3 and 9.

The above composition can be used to prepare orally administered products such as powders, granules, dry suspensions, tablets, effervescent tablets, capsules, lozenges, sustained-release preparations, drinks, beverages and oral solutions using conventional techniques.

Embodiment 3. A Powder or Dry Suspension Preparation or Granules Including the Present Invention Fructooligosaccharide 10-500 mg
L-Theanine 10-500 mg
L-Tryptophan 70 mg
Taurine 100 mg
Magnesium Citramate 1.5 g Vitamin B3 5 mg Vitamin B6 0.6 mg Vitamin B12 4.0 μg Lactose 2.8 g Flavouring and sweetener The fructooligosaccharide(s) may include one or more trisaccharide, tetrasaccharide, pentasaccharide, hexasaccharide, heptaasaccharide, octasaccharide and nonasaccharide sugar molecules, and may consist of FructoseN and/or Glucose-FructoseN where N is between 3 and 9.

Embodiment 4. A Suspension Preparation Containing Present Invention

Fructooligosaccharide 10-500 mg

L-Theanine 10-500 mg

Taurine 100 mg

Lactose 2.8 g

Flavouring and sweetener

The fructooligosaccharide(s) may include one or more trisaccharide, tetrasaccharide, pentasaccharide, hexasaccharide, heptaasaccharide, octasaccharide and nonasaccharide sugar molecules, and may consist of FructoseN and/or Glucose-FructoseN where N is between 3 and 9.

Effectiveness of the Invention in Standard Animal Tests

The effectiveness of the invention has been demonstrated by the following rigorous animal testing regimen as described below.

The Passive Avoidance Test (Solomon and Wynne, 1954; Solomon and Turner, 1960) is a fear-aggravated task employed to evaluate learning and memory in rodent models. In this test, subjects learn to avoid an environment in which an aversive stimulus (such as a foot-shock) was previously delivered. The test chamber is divided into a light compartment and a dark compartment, with a gate between the two. Animals are allowed to explore both compartments on the first day. On the following day, they are given a mild foot shock in one of the compartments. Animals will learn to associate certain properties of the chamber with the foot shock. In order to test their learning and memory, the mice are then placed back in the compartment where no shock was delivered. Mice with normal learning and memory will avoid entering the chamber where they had previously been exposed to the shock. This is measured by recording the latency to cross through the gate between the compartments. "Learning" is the period where mice were trained in this test (Table 1 and 2). Mice were tested at 24 or 48 hours after learning and the results were recorded ("Test column" in Table 1 and 2). "Fade" indicates re-testing of mice 5 days after learning ("Fade column" Table 1 and 2). Error percentage indicates the percentage of mice that have been shocked during the test.

Our research was undertaken with KumMing (KM) mice (Dai et al. 2012; Ma et al. 2013). In each test, 48 KM mice were separated into 4 groups, 12 mice per group. A negative-control group was also included in the test and mock treated. Our data indicate that neither fructooligoscharide nor L-theanine alone have a positive impact on rodent memory (Table 1). However, treatment of mice with a dose of embodiment 1, consisting of a combination of both fructooligoscharide and L-theanine, enhances memory in a statistically significant fashion in the mouse passive avoidance test (Table 1).

We subsequently, tested different doses of embodiment 1, 0.1, 0.2 or 0.3 g/kg of mouse body weight (bw) of embodiment 1, consisting of a combination of fructooligoscharide and L-theanine, in the passive avoidance test. Mice administered 0.2 g/kg.bw or 0.3 g/kg.bw of embodiment 1 (containing 0.134 g/kg.bw of L-theanine and 0.066 g/kg.bw of fructooligosaccahride or 0.201 g/kg.bw of L-theanine and 0.099 g/kg.bw of fructooligosaccahride, respectively) showed a statistically significant reduction in error count (p<0.01) (Table 2). Thus, our data indicates that doses of 0.2 g/kg.bw and 0.3 g/kg.bw of embodiment 1, compromised of a combination of both fructooligosaccahride and L-theanine, enhances memory in a statistically significant fashion in the mouse passive avoidance test.

To confirm and extend these findings, we also determined if different doses of embodiment 1, compromised of a combination of both fructooligosaccahride and L-theanine, could positively impact memory in an alternative assay, the Morris water maze test (D'Hooge, R. and De Deyn, P. P. 2001; Vorhees, C. and Williams, M. 2006). This test is designed to test both spatial memory and long-term memory by observing and recording escape latency, thigmotaxis duration, distance moved and velocity during the time spent in the test tank. Tempera paint is added into the water until it becomes opaque. A hidden platform, $\frac{1}{10}$ the length of the diameter of the water body, is placed about 1 cm below the water surface. Three fourths of the water tank is surrounded by privacy blinds with 3 visual cues. The subjects are monitored by a video tracking system directly above the water tank as they swim and parameters are measured using Ethovision software. "Learning" is the period where mice are trained in this test (Table 3). Mice were tested 24 hours after learning and the results recorded ("Test column" in Table 3). The "Fade" column indicates re-testing of mice 5 days after learning (Table 3). The percentage of mice that finished the maze was also recorded (Table 3).

Our research was undertaken with K M mice (Dai et al. 2012; Ma et al. 2013). In each test, 48 KM mice were separated into 4 groups, 12 mice per group. A negative-control group was also included in the test and mock treated. Our data indicate that mice in all groups (0.1, 0.2 or 0.3 g/kg.bw of embodiment 1, containing 0.067, 0.134 or 0.201 g/kg.bw, respectively, of L-theanine and 0.033, 0.066 and 0.099 g/kg.bw, respectively, of fructooligosaccharide) show a statistically significantly reduction in the time to finish this test. Thus, indicating embodiment 1, containing a combination of fructooligosaccharide and L-theanine, enhances memory, as determined by the Morris water maze test.

Effectiveness of the Invention in a Human Clinical Trial

To confirm and extend our findings that an embodiment consisting of both oligofructosaccharide and L-theanine can enhance memory in two distinct classical mouse models designed to test this capacity, we undertook an independent, double-blind, 30-day clinical trial. This was employed to determine if this embodiment can also enhance human memory and or associated brain function. Thus, 120 healthy adults, 35 males and 81 females, were recruited voluntarily to participate. Of these recruits, 116 participants completed the trial. The Clinical Memory Scale was used to assess participants' memory throughout the trial, following Technical Standards for Testing and Assessment of Health Food (2003) (Table 4-8).

Clinical memory, associative learning, graphic memory, the recognition of meaningless images and portrait retrieval are different individual memory tests that were conducted during the trial (He et al., 2008).

In the clinical memory test, the examinee reads 24 words, in which 12 of them belongs to the same category while the other 12 words are not associated with the given category. The examinee is then asked to recall the 12 words that belong to the same category. In the associative learning test, the examinee reads 12 word pairs, in which 6 of them are semantically related, with random order, 3 times. The examinee is subsequently given the first word of the pair and asked to recall the second. In the graphic memory test, the examinee is given 2 sets of pictures, with each set containing 15 pictures. They are then asked to recall the pictures within 2 minutes. In the recognition of meaningless images test, the examinee is shown 20 pictures with 5 different patterns of drawing. Afterwards, the examinee is shown a further 40 pictures to recall if they have seen the same pattern in the first 20 pictures. In the portrait retrieval test, the examinee is shown 6 human portraits and the associated name of the individual, their occupation and characteristics. The examinee is subsequently asked to recall the name, occupation and habit of the person while shown the relevant portrait, although the order of portraits is changed (He et al. 2008). Total memory measurement is a combined score of individual scores derived from the above individual tests. The memory quotient is calculated using total memory measurement according to the equivalent memory quotient conversion table. Memory quotient is the benchmark for human memory.

Firstly, memory was compared between participants separated into either the placebo group or the treatment group before commencement of the clinical trial. No statistically significant difference could be detected in clinical memory, associative learning or graphic memory in either the placebo or the treatment group before the onset of the clinical trial (Table 4). Thus, establishing an indistinguishable baseline memory between the subsequent placebo group and treatment group to be utilised in the clinical trial.

Importantly, the placebo group showed no increase in memory during the duration of the clinical trial (Table 5). In contrast, participants who were administered the present invention showed statistically significant improvement in memory test scores, indicating the present invention can enhance human memory. This was evidenced by a series of well-established memory indicators. Participants who were administered the present invention showed statistically significant improvement in clinical memory, associative learning, graphic memory, the recognition of meaningless images and portrait retrieval (Table 6 and 7). Thus, administration of the current invention to participants enhanced the performance of human memory, as scored by multiple indicators.

To confirm and extend these findings we next scored the participants in this clinical trial for possible enhancement of memory quotient and total memory measurement following administration of the current invention. Both memory quotient and total memory measurement exhibited striking statistically significant enhancement following administration of the current invention (Table 8).

TABLE 1

A combination of both fructooligosaccharide and L-theanine but not
each molecule alone enhances memory in the passive avoidance test

| Dose (g/kg · bw) | Number of Mice | Learning Incubation period (Sec) | Learning Error Count | Test Incubation period (Sec) | Test Error Count | Fade Incubation period (Sec) | Fade Error Count |
|---|---|---|---|---|---|---|---|
| Control | 12 | 52.60 ± 16.52 | 3.00 ± 1.83 | 214.56 ± 59.15 | 2.20 ± 1.32 | 227.60 ± 43.56 | 1.84 ± 1.14 |
| 0.01 Embodiment 1 | 12 | 39.20 ± 14.99 | 2.70 ± 1.88 | 248.82 ± 75.27 | 0.80 ± 0.79* | 318.00 ± 53.06 | 0.35 ± 0.33* |
| 0.0067 L-Theanine | 12 | 48.30 ± 10.71 | 3.90 ± 1.52 | 232.13 ± 70.71 | 1.22 ± 1.14 | 267.80 ± 51.03 | 1.40 ± 1.07 |
| 0.0033 Fructooligosaccharide | 12 | 49.62 ± 12.86 | 4.02 ± 1.93 | 230.30 ± 72.63 | 1.76 ± 1.01 | 241.30 ± 43.26 | 1.50 ± 0.99 |

Passive avoidance test to demonstrate activity of present invention. Mice administered with 0.01 g/kg · bw embodiment 1 (containing 0.0067 g/kg · bw L-theanine and 0.0033 g/kg · bw true tooligosaccahride) showed statistically significant less (indicated as *p < 0.05) errors in passive avoidance test comp are to fructooligosaccharide, L-theanine and the control group, Neither L-theanine or fruictooligosaccahride alone showed any sstatistically significant impact on memory enhancement.

TABLE 2

Different doses of both fructooligosaccharide and L-theanine
enhance memory in the mouse passive avoidance test

| Dose (g/kg · bw) | Number of Mice | Learning Incubation period (Sec) | Learning Error Count | Test Incubation period (Sec) | Test Error Count | Fade Incubation period (Sec) | Fade Error Count | Error Percentage (%) Learning | Test | Fade |
|---|---|---|---|---|---|---|---|---|---|---|
| Control | 12 | 64.58 ± 49.48 | 2.58 ± 1.31 | 165.42 ± 141.02 | 0.83 ± 0.94 | 242.17 ± 58.39 | 1.00 ± 0.95 | 100.00 | 50.00 | 41.67 |
| 0.1 | 12 | 67.33 ± 36.42 | 3.58 ± 1.88 | 169.08 ± 122.12 | 1.00 ± 1.13 | 288.83 ± 38.68 | 0.08 ± 0.29 | 100.00 | 58.33 | 8.33 |
| 0.2 | 12 | 84.67 ± 76.86 | 3.00 ± 1.65 | 178.08 ± 111.09 | 1.58 ± 1.44 | 280.75 ± 66.68 | 0.08 ± 0.29 ** | 91.67 | 66.67 | 8.33 |
| 0.3 | 12 | 67.42 ± 59.32 | 3.42 ± 1.62 | 171.33 ± 124.31 | 1.33 ± 1.30 | 271.92 ± 78.35 | 0.17 ± 0.39 ** | 100.00 | 58.33 | 16.67 |

Passive avoidance test to demonstrate activity of present invention. As expected, in learning and testing stage, mice administered with different doses of the present invention showed no difference compared to the control group (p > 0.05). In memory reproduction stage, however, mice administered of 0.2 g/kg · bw and 0.3 g/kg · bw embodiment 1 (containing 0.134 g/kg · bw L-theanine and 0.066 g/kg · bw fructooligosaccahride, 0.201 g/kg · bw L-theanine and 0.099 g/kg · bw fructooligosaccahride respectively) showed less error count (indicated as **p < 0.01). Thus, indicating embodiment 1 improves memory in a rodent model system.

40

TABLE 3

A combination of both fructooligosaccharide and
L-theanine enhance memory in the Morris water maze test

| Dose (g/kg · bw) | Number of Mouse | Learning (5 times) Total time to finish maze (Sec) | Learning Error Count | Test Time to finish maze (Sec) | Test Error Count | Reproduction Time to finish maze (Sec) | Reproduction Error Count | Percentage of mouse that finish maze in 2 min (%) Learning (5 times) | Test | Fade |
|---|---|---|---|---|---|---|---|---|---|---|
| Control | 12 | 281.67 ± 88.84 | 12.17 ± 4.26 | 91.08 ± 36.18 | 4.67 ± 2.61 | 78.83 ± 35.22 | 2.83 ± 1.34 | 83.33 | 50.00 | 75.00 |
| 0.1 | 12 | 253.83 ± 85.18 | 12.92 ± 4.58 | 67.67 ± 38.13 | 3.08 ± 1.98 | 39.00 ± 15.27 * | 1.33 ± 0.89 | 86.67 | 83.33 | 100.00 |
| 0.2 | 12 | 211.17 ± 88.91 | 10.33 ± 4.27 | 58.83 ± 32.99 | 2.42 ± 1.93 | 47.17 ± 20.83 * | 2.33 ± 1.56 | 95.00 | 91.67 | 100.00 |
| 0.3 | 12 | 229.00 ± 52.61 | 9.75 ± 3.96 | 82.83 ± 37.30 | 3.17 ± 1.64 | 63.25 ± 37.81 * | 2.67 ± 2.15 | 91.67 | 58.33 | 75.00 |

Morris water maze test to demonstrate activity of present invention. As expected, at the learning and testing stage, mice administered with different doses of the present invention show no difference compared to the control group (p > 0.05). However, in the memory reproduction stage, mice in all groups (0.1/0.2/0.3 g/kg · bw of embodiment 1, containing 0.067/0.134/0.201 g/kg · bw of L-theanine and 0.033/0.066/0.099 g/kg · bw of fructooligosaccharide) showed statistically significant less time to finish the maze (indicated as * p < 0.05). Thus, indicating embodiment 1 improves memory in a rodent model system.

TABLE 4

No significant difference in memory scores of participants
separated into either a placebo group or a treatment
group before commencement of an independent, double-blind, clinical trial

| Group | Number of participants | Clinical Memory | associative learning | Graphic memory | The recognition of meaning-less images | Portrait retrieval |
|---|---|---|---|---|---|---|
| Placebo | 58 | 13.17 ± 3.38 | 13.97 ± 2.88 | 13.83 ± 3.65 | 14.66 ± 3.21 | 14.50 ± 2.36 |
| Treatment | 58 | 13.71 ± 3.23 | 13.41 ± 3.33 | 13.72 ± 3.83 | 14.41 ± 3.08 | 14.16 ± 2.67 |

Memory scores of participants separated into a placebo group or a treatment group before commencement of a clinical trial. There was no difference in clinical memory, associative learning or graphic memory between these two groups in the absence of any treatment or placebo before initiation of the clinical trial.

TABLE 5

No memory enhancement in the placebo group during a clinical trial

| Group | Number of participants | Clinical Memory | associative learning | Graphic memory | The recognition of meaning-less image | Portrait retrieval |
|---|---|---|---|---|---|---|
| Before | 58 | 13.17 ± 3.38 | 13.97 ± 2.88 | 13.83 ± 3.65 | 14.66 ± 3.21 | 14.50 ± 2.36 |
| After | 58 | 13.12 ± 2.93 | 13.81 ± 2.29 | 14.17 ± 2.71 | 14.50 ± 2.96 | 14.00 ± 1.84 |

Memory score of participants in placebo group before and al ter trial. Participants in the placebo group showed no changes in memory score before and after trial, indicating the placebo has no effect on memory improvement.

TABLE 6

Treatment with embodiment 1 enhances human memory in a clinical trial

| Group | Number of participants | Clinical Memory | associative learning | Graphic memory | The recognition of meaning-less image | Portrait retrieval |
|---|---|---|---|---|---|---|
| Before | 58 | 13.71 ± 3.23 | 13.41 ± 3.33 | 13.72 ± 3.83 | 14.41 ± 3.08 | 14.16 ± 2.67 |
| After | 58 | 14.60 ± 2.67 ** | 14.34 ± 2.82 | 17.33 ± 3.10 ** | 15.03 ± 2.77 ** | 15.12 ± 2.30 ** |

Memory score of participants in treatment group before and after clinical trial. Participants who were administered the present invention (0.52 g/person/day of embodiment 1, containing 0.36 g L-theanine and 0.18 g fructooligosaccharide) showed statistically significant improvement in memory test scores (indicated as ** $p < 0.01$ compared to before trial), indicating the present invention can improve human memory, as evidenced by a number of well-established indicators.

TABLE 7

Administration of embodiment 1 enhances human memory relative to administration of a placebo

| Group | Number of participants | Clinical Memory | associative learning | Graphic memory | The recognition of meaning-less image | Portrait retrieval |
|---|---|---|---|---|---|---|
| Placebo | 58 | 13.12 ± 2.93 | 13.81 ± 2.29 | 14.17 ± 2.71 | 14.50 ± 2.96 | 14.00 ± 1.84 |
| Treatment | 58 | 14.60 ± 2.67 ** | 14.34 ± 2.82 | 17.33 ± 3.10 ** | 15.03 ± 2.77 | 15.12 ± 2.30 ** |

Memory scores of participants in both placebo group and treatment group after trial. Participants who were administered the present invention (0.52 g/person/day of embodiment 1, containing 0.36 g L-theanine and 0.18 g fructooligosaccharide) improved performance (indicated as ** $p < 0.01$ compared placebo group after trial), indicating the present invention can improve memory, as evidenced by a number of well-established indicators.

TABLE 8

Comparison of total memory measurement and memory quotient of participants before and after administration of the current invention

| Group | Embodiment 1 (n = 58) | | Placebo (n = 58) | |
| | Before trial | After trial | Before trial | After trial |
|---|---|---|---|---|
| Total measurement | 69.41 ± 6.63 | 76.43 ± 5.68 **^^ | 70.12 ± 6.79 | 69.60 ± 6.37 |
| Memory quotient | 80.12 ± 7.24 | 85.98 ± 6.59 **^^ | 82.67 ± 7.17 | 82.31 ± 6.85 |

Comparison of total memory measurement and memory quotient. Participants who were administered the present invention (0.52 g/person/day of embodiment 1, containing 0.36 g L-theanine and 0.18 g fructooligosaccharide) showed a statistically significant enhancement in both memory score and memory quotient, compared to participants in a placebo group after the clinical trial (indicated as **, $p < 0.01$). Further, there is a statistically significant enhancement in both memory score and memory quotient of participants following administration of the invention (indicated as ^^, $p < 0.01$). Thus, the present invention can improve both total memory measurement and memory quotient.

A series of safety tests have also been conducted to demonstrate the safety of the invention. These include the acute oral toxicity test (Walum, 1998; OECD 2001), repeated dose 28-day oral toxicity test (OECD, 2008) and the genetic toxicity test (Proudlock, 2016). The resulting data suggest that our invention composition is non-toxic and safe to consume. The acute oral toxicity test indicates that the $LD_{50}$ (median lethal dose) is >10 g/kg.bw. From a repeated dose 28-day oral toxicity test, the harmful dose of the present invention was established at larger than 2.47 g/kg.bw. Three independent tests were conducted for genetic toxicity, including the Bacterial Reverse Mutation Assay (Ames test), In Vivo Rodent Micronucleus Assay and The In Vitro Chromosome Aberration Test (Proudlock., 2016). The resulting findings from all three test indicate no genetic toxicity was associated with the present invention.

In conclusion, collectively, our findings show that neither fructooligosaccharides nor L-theanine improved mammalian memory in a series of well-established memory tests in a rodent model. However, a composition containing both fructooligosaccharides and L-theanine enhanced mammalian memory in a statistically significantly fashion in a series of rodent memory tests. To confirm extend these findings, we undertook an independent, double-blind, clinical trial to determine if this composition of fructooligosaccharides and L-theanine could positively impact human memory. Participants who were administered the present invention showed a statistically significant improvement in clinical memory, associative learning, graphic memory, the recognition of meaningless images and portrait retrieval. Furthermore, both memory quotient and total memory measurement also exhibited a statistically significant enhancement following administration of the current invention. Therefore, the current invention enhances human memory, as scored by multiple indicators.

Furthermore, to test the hypothesis that administration of M. officinalis FOS and L-theanine in a ratio of about 2:1 L-theanine:FOS synergistically enhance mice memory, we have performed a step-down passive avoidance test and a water maze test. This was employed to assess the effect of M. officinalis FOS and L-theanine individually on mice memory compared to their collective effect when administrated in combination in a ratio of about 2:1 L-theanine:FOS (MT-01) (FIG. 1).

In the step-down passive avoidance test, neither the FOS-only nor L-theanine-only group show any significant difference in latency during the retention phase compared to the control group at a low dose.

in contrast, mice treated with the mentioned MT-01 combination showed a significantly longer (p<0.05, FIG. 1c) latency in the retention phase compared to individual treatments and control data.

In addition, mice treated with the MT-01 combination showed significantly less error during the passive avoidance test compared to individual treatments and control data (p<0.01, FIG. 1d).

*In addition, mice treated with FOS alone showed a statistically significant higher latency and less error compared to the control group, but only at a high dose (p<0.05, FIGS. 1c and d).

*Also, the administration of L-theanine alone showed less error and higher latency in a passive avoidance test at high dose (FIGS. 1c and 1d).

*Administration of MT-01 at a low and medium dose showed significantly longer latency compared to all other test groups, but at a high dose, the performance of mice administrated with MT-01 showed no statistical difference compared to other treatment groups, although significantly better than the control group, during the retention phase.

With regard to error count (FIG. 1c), administration of MT-01 in a medium dose showed significantly less error during the testing phase compared to all other groups. Administration of MT-01 in a low and high dose resulted in significantly less error compare to the FOS treatment group, but is not significantly different to the L-theanine group (FIG. 1d).

Maze test was performed to further confirm the hypothesis.

Compared to control group, all mice with MT-01, L-theanine or FOS treatment at all doses exhibited significantly (p<0.05) less time to escape during the test (FIG. 1a). In addition, mice administrated with MT-01 show a significantly reduced escape time compared to other groups in the retention phase (p<0.05, FIG. 1a). —At a medium and high dose, no significant differences were observed in escape time between mice treated with MT-01, L-theanine or FOS in escape time during test.

Mice treated with a low dose of MT-01 showed a significantly reduced error count in a maze test during the testing phase, compared to all other groups (FIG. 1b). However, all other groups showed no significant difference compared to the control group or between each other (FIG. 1b).

We analysed the synergy between FOS and L-theanine in the formulation by calculating the coefficient of drug interaction (CDI), as shown in Table 1.

TABLE 1

| Coefficient of drug interaction between FOS and L-theanine in passive avoidance test and water maze test. | | | | | | | | | |
|---|---|---|---|---|---|---|---|---|---|
| | | | Passive avoidance test | | | | Water maze test | | | |
| Dose(mg/kg · bw) | | | Error count during testing phase | | | | Error count during testing phase | | | |
| Group | L-theanine | FOS | L-theanine | FOS | MT-01 | CDI | L-theanine | FOS | MT-01 | CDI |
| | 0 | 0 | 2.33 | 2.33 | 2.33 | | 4.11 | 4.11 | 4.11 | |
| Low | 66 | 33 | 0.83 | 1.25 | 1.75 | 0.89 | 2.45 | 3.83 | 3.77 | 0.70 |
| Medium | 134 | 66 | 1.00 | 1.92 | 1.83 | 0.33 | 2.95 | 2.98 | 2.84 | 1.44 |
| High | 200 | 100 | 0.50 | 1.08 | 1.00 | 1.08 | 2.41 | 2.98 | 2.25 | 1.47 |

Table 1. Coefficient of drug interaction between FOS and L-theanine in passive avoidance test and water maze test.

Table 1 depicts the Coefficient of drug interaction (CDI) between FOS and L-theanine on error counts in water maze test during retention phase. CDI suggests L-theanine and FOS act antagonistically (CDI>1) at high doses in the passive avoidance test (CDI=1.08) and a medium dose (CDI=1.44) and a high dose (CDI=1.47) in the water maze test. L-theanine and FOS act synergistically (CDI<1) at a low dose in both tests, where CDI is 0.89 and 0.70, respectively.

Thus, our data suggests that, during the passive avoidance test, at low (66 mg/kg L-theanine and 34 mg/kg FOS in combination) and medium (134 mg/kg L-theanine and 66 mg/kg FOS) doses, L-theanine and FOS act synergistically (CDI<1) in enhancing mouse memory, resulting in a reduced error count during the testing phase.

However, L-theanine and FOS may act antagonistically (CDI>1) at high (200 mg/kg L-theanine and 100 mg/kg FOS) doses. Similar results were obtained in the maze test, L-theanine and FOS act synergistically at a low dose, resulting in lower errors during the testing phase and act antagonistically at medium and high doses.

By translating the above dosages from Animal experiment to Human, based on "Nair A B, Jacob S. A simple practice guide for dose conversion between animals and human. J Basic Clin Pharm. 2016; 7(2):27-31. doi:10.4103/0976-0105.177703", the effective low dose (66 mg/kg L-theanine and 34 mg/kg FOS, 100 mg/kg total) and medium dose (200 mg/kg total) observed to show synergy in the animal test (Mice), convert, by calculation, into a human effective dose (HED) of from 427 mg/day to 854 mg/day of composition with 1:2 ratio between FOS and L-theanine. These doses are very close to the range we have found to show surprising synergic effects as compared to employing L-theanine or OS separately. Our example is also 520 mg/person/day, which is in that range.

To summarize, we have demonstrated that FOS isolated from *M. officinalis* and L-theanine act synergistically at a low dose to enhance mice memory in the maze test and also act synergistically at low and medium doses to enhance mice memory in the passive avoidance test. In both tests, FOS and L-theanine appear to act antagonistically at a high dose.

REFERENCES

Baddeley, A. D. (1966). Q. J. Exp. Physiol. 18 (4): 302-9.

Ballard, C., Gauthier, S., Corbett, A., Brayne, C., Aarsland, D., Jones, E. (2011). Lancet. 377 (9770): 1019-31.

Burns, A. and Iliffe, S. (2009). BMJ. 338: b75.

Cowan, N. (2001). Behaviourial Brain Sciences. 24 (1): 87-114, discussion 114-85.

D'Hooge, R. and De Deyn, P. P. (2001). Brain Research, Brain Research Reviews. 36, 60-90.

Dai, Y., Cui, J., Cun, Y., et al. (2012). Journal of Surgical Research 176: e65-e71.

Dietz, C. and Dekker, M. (2017). Current Pharmaceutical Design 23, 2876-2905.

Eysenck, M. (2012). Attention and Arousal: Cognition and Performance. Berlin, Heidelberg: Springer Berlin.

Hardy, J. (1997) Trends Neuroscience 20, 154-159.

He, F., Guan, H., Zhao, Z., Miao, X., Zhou, Q., Li, L., Huang, D., Liu, A. and Miao, D. (2008). Stereotactic and Functional Neurosurgery, 86(5), 320-329.

Hidese, S., Ota, M., Wakabayashi, C., Noda, T., Ozawa, H., Okubo, T. and Kunugi, H. (2017). Acta Neuropsychiatr 29, 72-9.

LaBar K. S. and Cabeza R. (2006). Nature Reviews Neuroscience. 7 (1): 54-64.

Ma, P., Wu, Y., Zeng, Q., et al. (2013). Food Chemistry and Toxicology. 58, 177-183.

OECD Guidelines for The Testing of Chemicals (2008). Repeated Dose 28-Day Oral Toxicity Study in Rodents, OECD/OCDE 407.

OECD Guidelines for The Testing of Chemicals (2001). Acute Oral Toxicity-Fixed Dose Procedure, OECD/OCDE 420.

Proudlock, R. (2016). Genetic Toxicology Testing: A Laboratory Manual. Academic Press.

Schacter D L, Gilbert D T, Wegner D M (2009). "Semantic and episodic memory". Psychology. pp. 185-6. ISBN 9780716752158.

Sherwood, L. (2015). Human Physiology: From Cells to Systems. Cengage Learning. pp. 157-162. ISBN 978-1-305-44551-2.

Smith, A. P., Sutherland, D. and Hewlett, P. (2015) Nutrients 7, 8887-8896.

Solomon, R. L. and Turner, L. H. (1960). Science 132, 1,499-1,500.

Solomon, R. L., and Wynne, L. C. (1954). Psychological Review 61, 353-385.

Staniloiu, A. and Markowitsch, H. J. (2012). "The Remains of the Day in Dissociative Amnesia". Brain Sciences. 2 (2): 101-129.

Vorhees, C. and Williams, M. (2006). Nature Protocols 1, 848-858.

Walum E. (1998). Environmental Health Perspectives, 106 Suppl2, 497-503.

Xin, Y., Diling, C., Jian, Y., Ting, L., Guoyan, H., Hualun, L., Xiaocui, T., Guoxiao, L., Ou, S., Chaoqun, Z., et al. (2018). Frontiers in Neurology 9, 412.

17
18

Yin, C., Gou, L., Liu, Y., Yin, X., Zhang, L., Jia, G., and Zhuang, X. (2011). Phytotherapy Research 25, 1636-1639.

The invention claimed is:

1. A composition consisting of: L-theanine, one or more fructooligosaccharides and optionally pharmaceutically acceptable excipients, wherein the weight ratio of the L-theanine to the one or more fructooligosaccharides is about 2:1, wherein the composition is formulated to deliver a combined dose of the L-theanine and the one or more fructooligosaccharides of about 520 to 900 mg/person/day and is administered to enhance memory in humans.

2. The composition according to claim 1, wherein the one or more fructooligosaccharides comprise between 3 and 9 fructose residues.

3. The composition as claimed in claim 1, wherein the one or more fructooligosaccharides are extracted from *Morinda officinalis*.

4. The composition as claimed in claim 1, wherein the composition is in the form of a pharmaceutical composition.

5. The composition as claimed in claim 1, wherein the composition is in the form of a food or nutraceutical.

6. The composition as claimed in any one of claim 1, 4, or 5, wherein the composition is in the form of a powder, granules, suspension, tablet, capsule, lozenge, bakery item, sweets, drink, beverage or oral preparation.

7. The composition as claimed in claim 1, wherein the composition is in the form of an orally-administered product.

8. The composition as claimed in claim 7, wherein the orally-administered product is selected from the group consisting of: powders, granules, dry suspensions, tablets, capsules, lozenges, sustained-release preparations, drinks, beverages, oral solutions, and combinations thereof.

9. The composition as claimed in claim 1, wherein the one or more fructooligosaccharides comprises at least one fructose residue and at least one glucose residue.

10. The composition as claimed in claim 9, wherein the at least one fructose residue comprises D-fructose, and wherein the at least one glucose residue comprises D-glucose.

* * * * *